United States Patent [19]

Wedekind et al.

[11] Patent Number: 5,780,260
[45] Date of Patent: Jul. 14, 1998

[54] IMMOBILIZATION OF PENICILLIN G AMIDASE, GLUTARYL-7-ACA ACYLASE OR D-AMINOACID OXIDASE ON AN AMINOFUNCTIONAL ORGANOSILOXANE POLYMER CARRIER

[75] Inventors: Frank Wedekind, Penzberg; Adelheid Daser, Schlehdorf; Wilhelm Tischer, Peissenberg, all of Germany

[73] Assignee: Boehringer Mannheim GmbH, Mannheim-Waldhof, Germany

[21] Appl. No.: 648,015

[22] PCT Filed: Dec. 13, 1996

[86] PCT No.: PCT/EP94/04132

§ 371 Date: May 30, 1996

§ 102(e) Date: May 30, 1996

[87] PCT Pub. No.: WO95/16773

PCT Pub. Date: Jun. 22, 1995

[30] Foreign Application Priority Data

Dec. 15, 1993 [DE] Germany .......... 43 42 770.7

[51] Int. Cl.⁶ .......... C12P 37/00; C12P 35/00; C12N 11/18; C12N 11/14
[52] U.S. Cl. .......... 435/43; 435/44; 435/45; 435/47; 435/49; 435/50; 435/51; 435/175; 435/176; 435/177
[58] Field of Search .......... 435/175, 174, 435/176, 177, 181, 43, 44, 45, 47, 48, 49, 50, 51

[56] References Cited

FOREIGN PATENT DOCUMENTS 231093   8/1987   European Pat. Off. .
496993   8/1992   European Pat. Off. .

OTHER PUBLICATIONS

Danzig, et. al., Indian Journal of Chemistry, vol. 32 B, Jan. 1993, pp. 40-43.

Brink, et. al., Enzyme Microb. Technol., vol. 10, Dec. 1988, pp. 736-743.

*Primary Examiner*—David M. Naff
*Attorney, Agent, or Firm*—Nikaido Marmelstein Murray & Oram LLP

[57] ABSTRACT

An enzyme selected from penicillin-G amidase, glutaryl-7-ACA acylase and D-amino acid oxidase is immobilized by covalent bonding on an aminofunctional organosiloxane polymer carrier to provide an immobilized enzyme having a specific volume activity of at least 100 U/g wet carrier. Preferably, the carrier has an average diameter or 0.01 to 3 mm and is essentially spherical. Covalent bonding is accomplished by activating amino groups on the carrier with a dialdehyde and reacting the activated groups with reactive groups on the enzyme. An amount of enzyme is immobilized to provide a weight ratio of enzyme to carrier of 1 to 300 mg protein per g wet carrier.

23 Claims, 2 Drawing Sheets

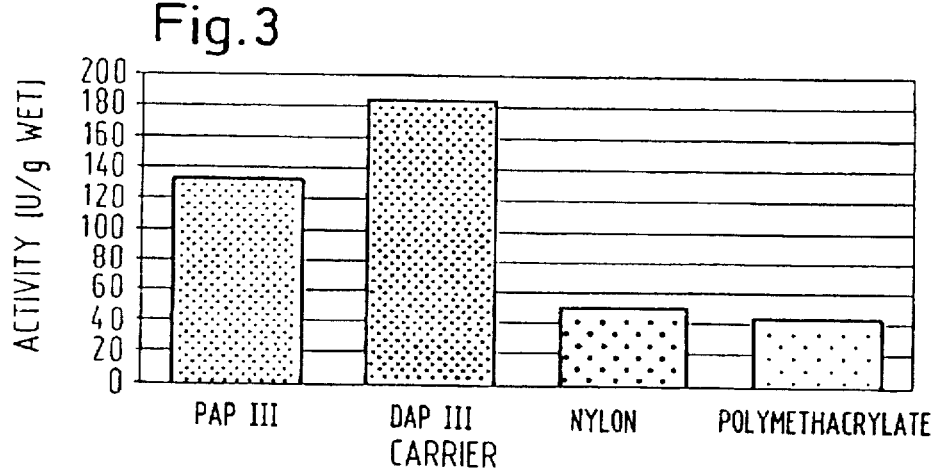
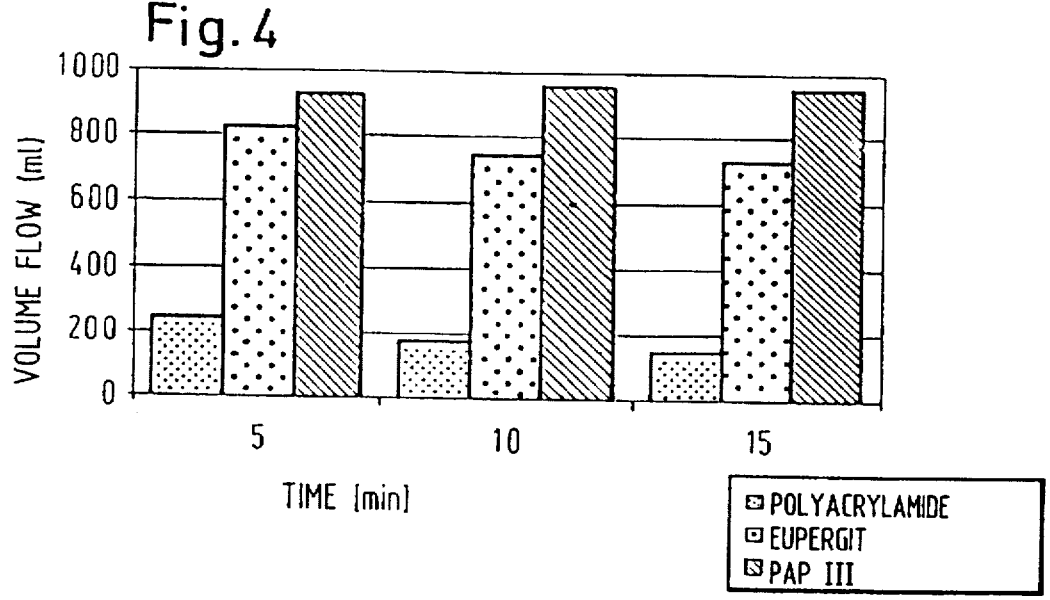
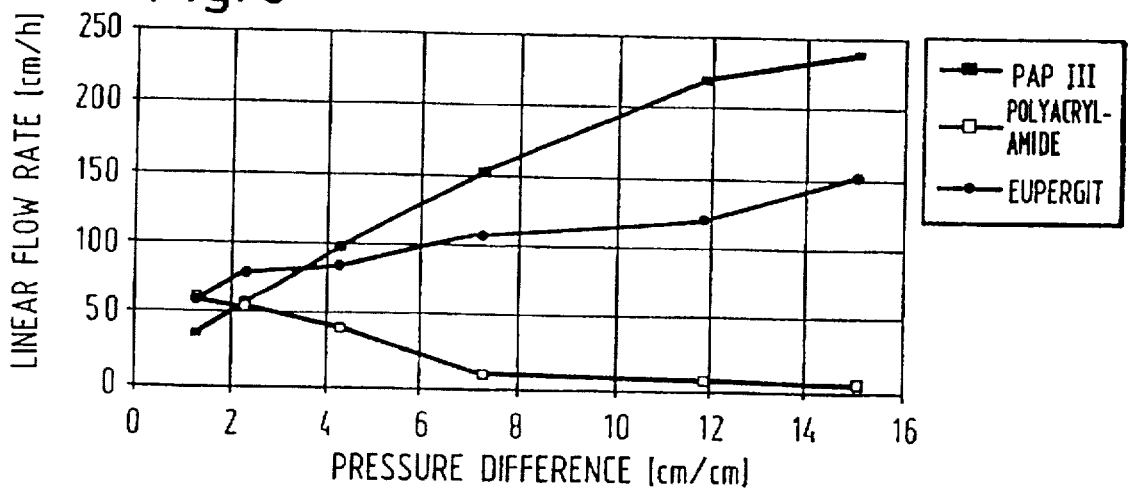

IMMOBILIZATION OF PENICILLIN G AMIDASE, GLUTARYL-7-ACA ACYLASE OR D-AMINOACID OXIDASE ON AN AMINOFUNCTIONAL ORGANOSILOXANE POLYMER CARRIER

The application is a 371 of PCT/EP94/04132, filed Dec. 13, 1994.

The present invention concerns enzymes immobilized on carriers selected from the group comprising penicillin-G amidase, glutaryl-7-ACA acylase and D-amino acid oxidase, the use of these enzymes in an enzymatic synthesis reaction as well as a process for improving the volume activity and stability of these enzymes immobilized on carriers.

The immobilization of biologically active substances, e.g. enzymes, on solid carrier materials can be carried out by numerous methods and is described in many monographs and publications (see e.g. Characterization of Immobilized Biocatalysts, Buchholz, K., (publisher), DECHEMA Monographs No. 1724–1731, vol. 84 (1979), Protein Immobilization - Fundamentals and Applications, Taylor R. F. (publisher), Marcel Dekker, Inc. (1991)). Apart from non-covalent immobilization techniques such as adsorption, entrapment, microencapsulation, chelation and aggregation, covalent immobilization methods have gained prominence for industrial applications.

Organic as well as inorganic materials of a synthetic or natural basis are known as carrier materials for immobilizing biologically active substances. The covalent immobilization of proteins on carrier materials is generally carried out by coupling the proteins via the reactive side chains of the amino acids to the carrier. A chemical activation of the carrier or/and the protein is usually necessary for this. The coupling chemistry is determined in each case by the type of protein as well as by the carrier matrix used. Due to the quite considerable differences in the secondary, tertiary and quarternary structures of proteins it is fundamentally impossible to predict the suitability of specific carrier materials for specific enzymes.

Organic carrier materials into which numerous reactive groups can be introduced have prevailed for most commercial applications for the immobilization of biologically active substances. Examples of these are natural polymers such as polysaccharide derivatives and structural proteins as well as synthetic macromolecular substances based on polystyrene or polyacrylate. These organic carrier materials can be activated by conventional chemical methods or already have reactive groups which enable linkages to be made with a protein to be immobilized. However, these organic carrier materials still have some disadvantages which limit their usability. Thus natural polysaccharide derivatives are often sensitive towards microbial degradation (cellulose), they have unfavourable particle properties (cellulose, fibres of different length) and poor mechanical or/and swelling properties.

Synthetic materials are usually insensitive towards microbial attack, but they have other disadvantages. Carrier materials based on polyacrylamide which are usually used in protein-monomer coimmobilizations are composed of potentially cancerogenic monomers (acrylamide) and exhibit a strong swelling in aqueous systems. Polyacrylates, polymethacrylates, hydroxyalkyl-methacrylates and polymethacrylamides can be prepared by polymerization of the appropriate monomers using suitable cross-linking agents and some are commercially available. Carriers that are already activated (e.g. Eupergit®, Biosynth®) can be produced from these materials, in particular by using glycidyl derivatives in copolymerizations or by subsequent modifications. These carrier materials exhibit a relatively strong swelling and often only low volume activities are achieved in the immobilization of enzymes which is why the use of these carrier materials is less suitable in enzymatic synthesis reactions.

Inorganic carriers exhibit much more favourable mechanical properties, thermal stability and resistance towards organic solvents and microbial attack than organic carriers. Examples of inorganic carriers are minerals such as bentonite, attapulgite and diatomaceous earth. They often exhibit a broad distribution of pore sizes. Non-porous materials such as metals and metal oxides usually only have small binding surfaces and are therefore in general unsuitable for the immobilization of biological substances. Controlled pore glass (CPG) can be manufactured with defined pore sizes and binding surfaces, but it is unstable under even moderately alkaline conditions (pH>8). Moreover, all inorganic materials mentioned so far must be pre-treated in a suitable manner before the actual coupling reaction and converted into an activated derivative. This derivatization is often relatively difficult due to the inert nature of the carrier. Most often the carrier is coated for this by silanization. Then the protein to be immobilized is generally covalently bound with 3-amino-propylethoxysilane after functionalizing the carrier. However, in this manner only low coupling yields of the protein are usually obtained.

The use of organo-functionalized polysiloxanes as enzymatic carriers is known (see e.g. Poster No. 518 and 519, "DECHEMA-Tagung der Biotechnologen 1992; Poster 5.218 "DECHEMA-Jahrestagung der Biotechnologen 1993).

Here it is described that organofunctional polysiloxanes, in particular aminofunctional polysiloxanes, can be used as carrier materials to immobilize the enzymes invertase, lactase and glucose oxidase. These enzymes are described as having a high binding capacity and binding effectiveness as well as an increased stability. An increase in the volume activity of the immobilized enzymes compared to other carrier materials is not disclosed.

The enzymes penicillin-G amidase, glutaryl-7-ACA acylase and D-amino acid oxidase are used for the industrial production of modified penicillin and cephalosporin antibiotics. D-Amino acid oxidase and glutaryl-7-ACA acylase catalyze a two-step enzymatic conversion of cephalosporin-C or derivatives or salts thereof into 7-aminocephalosporanic acid (7-ACA) or derivatives thereof (see e.g. EP-B-0 211 033, EP-A-0 409 521). Penicillin-G amidase catalyzes the synthesis of cefalotin from 7-ACA and thienylacetic acid.

When these above reactions are carried out on an industrial scale the said enzymes are usually used in an immobilized form. EP-B-0 211 033 describes for example the purification of D-amino acid oxidase from the microorganism Trigonopsis variabilis and the immobilization of this enzyme on CNBr-activated Sepharose in which a volume activity of 7 U/ml carrier material is obtained.

EP-A-0 492 495 discloses the immobilization of D-amino acid oxidase on a copolymer which is composed essentially of vinyl acetate and/or vinyl alcohol units and units of a cross-linking agent. A volume activity of 32 U/g wet carrier is obtained. The immobilized enzyme is stable for 6 months at 30° C. When other solid carriers are used (BrCN-activated Sepharose®, vinyl Sepharose and Eupergit®) lower volume activities and stabilities are obtained.

EP-A-0 496 993 describes the immobilization of D-amino acid oxidase from Rhodotorula gracilis and glutaryl-7-ACA acylase from Acinetobacter species which was produced in transformed E. coli cells, on a number of solid carriers e.g. strongly basic polystyrene resins with quarternary amino functional groups such as Amberlite® IFA900, weakly basic polystyrene resins with primary amino functional groups such as Duolite® A365, moderately basic poly-condensed phenolformaldehyde resins with secondary and tertiary amino functional groups such as Duolite® A568 or Duolite® A7. A volume activity for the D-amino acid oxidase of up to maximally 75 U/g wet carrier (epoxide-functionalized Eupergit® C) is described. A maximum volume activity of 41 U/g wet carrier (epoxide-functionalized Eupergit® C) is described for glutaryl-7-ACA acylase.

WO90/12110 discloses the immobilization of D-amino acid oxidase and glutaryl-7-ACA acylase on a silicon oxide-polyvinyl chloride composite in a lamellar form which can be derivatized with polyethylenimine and glutaraldehyde. An increase in the volume activity by this type of immobilization compared to other carrier materials is not described.

The literature references Wood et al. (J. Biotech. 13 (1990), 305–314) and Cobbs et al. (Biotechnology Techniques, Vol. 4, No. 1 (1990), 5–10) describe the immobilization of D-amino acid oxidase on a solid carrier with the aid of a trifunctional aziridine. An increase in the volume activity by this type of immobilization compared to other carrier materials is not described.

The literature reference Szwajcer-Dey et al. (Appl. Biochem. Biotech. 27 (1991), 239–250) describes the immobilization of D-amino acid oxidase from Trigonopsis variabilis on metal oxide particles and on CNBr-activated Sepharose. An immobilization of 23 mg D-amino acid oxidase per g wet Sepharose is described. An increase in the volume activity by the use of metal oxide carrier particles is not disclosed.

SUMMARY OF THE INVENTION

The object of the present invention was therefore to provide new enzymes immobilized on carriers selected from the group comprising penicillin-G amidase, glutaryl-7-ACA acylase and D-amino acid oxidase which have a higher volume activity or/and stability compared to known enzymes immobilized on carriers. A further object of the present invention was to provide a uniform carrier system for the three aforementioned enzymes which considerably simplifies the simultaneous use of these enzymes in enzymatic synthesis reactors.

The object according to the invention is achieved by providing enzymes immobilized on carriers selected from the group comprising penicillin-G amidase (E.C. 3.5.1.11), glutaryl-7-ACA acylase and D-amino acid oxidase (E.C.1.4.3.3) which is immobilized by a covalent binding to an aminofunctional organosiloxane polymer carrier material.

The term "aminofunctional organosiloxane polymer" according to the present invention encompasses polymeric compounds in which silicon atoms and if desired, titanium, zirconium or/and aluminium atoms are linked via oxygen atoms and free valencies of these metal atoms are saturated by organic residues which contain amino groups that can be activated. The amino groups are preferably primary amino groups. Such aminofunctional organosiloxanes are commercially available e.g. from the DEGUSSA AG Company, Frankfurt, Germany under the name DELOXAN®. The composition and production of preferred aminofunctional organosiloxanes is described for example in DE-OS 31 20 214, (U.S. Pat. No. 4,455,415) DE-OS 38 37 418, (U.S. Pat. No. 5,003,027) DE-OS 39 25 359 (U.S. Pat. No. 5,484,859) and DE-OS 39 25 360 (U.S. Pat. No. 5,093,451) to the disclosure of which reference is hereby made.

Examples of suitable functional amino groups on the organosiloxane polymers are e.g. $—NH_2$, $—RNH_2$, $—NH—R—NH_2$ or $—R—(NH—R')_n—NH_2$ in which R and R' can for example be, independently of one another, a linear or branched alkylene group with 1 to 10 C atoms, a cycloalkylene group with 5 to 8 C atoms or a linear or branched alkylene group which contains a cyclohexylene or phenylene unit. Particularly preferred examples of functional amino groups are $—NH_2$, $—NH(CH_2)_2—NH_2$, $—(CH_2)_3—NH_2$ or $—(CH_2)_2—NH—(CH_2)_2—NH—(CH_2)_2—NH_2$.

The aminofunctional carrier material can be any desired shape or form. However, particulate carrier materials of a suitable size which on the one hand have a high specific surface and on the other hand enable a good handling are preferred. A preferred average diameter range for the particles is 0.01 to 3 mm. The carrier material is preferably essentially spherical. The production of spherical aminofunctional organosiloxane polymers is described in the aforementioned DE-OS 39 25 359 and DE-OS 39 25 360 to the disclosure of which reference is hereby made. An average particle size of the carrier material of 0.05 to 1 mm is preferred and an average particle size of 0.1 to 0.4 mm is particularly preferred. An average particle size of 0.1 to 0.3 mm is preferred most for penicillin-G amidase and of 0.2 to 0.4 mm for glutaryl-7-ACA acylase and D-amino acid oxidase.

The capacity (i.e. the number of amino groups) of the aminofunctional carrier used to immobilize the enzymes is preferably 0.5–5 mval/g carrier, particularly preferably 1–4 mval/g carrier.

Various methods known from the state of the art can be used to immobilize the enzymes on the aminofunctional carrier. These methods usually comprise an activation of the amino groups located on the carrier by an activation reagent. The activated groups on the carrier can then subsequently react with reactive groups of the enzyme, in particular with amino groups in the side chain. Enzymes immobilized on carriers are obtained in this manner which surprisingly have an increased volume activity compared to other carrier materials.

The amino group of the carrier can be converted into a reactive isothiocyanate group by reaction with thiophosgene or 1,4-phenylene diisothiocyanate. Reaction of the carrier with dianhydrides (e.g. succinic acid anhydride) enable carboxyl functional groups to be introduced which can be converted into reactive acid chlorides and esters (e.g. N-hydroxysuccinimide esters). In addition the amino group on the carrier can be activated by reaction with chlorotriazines (e.g. cyanuric chloride). A further example of the activation is a reaction of primary amino groups on the carrier with 4-nitrobenzoyl chloride and diazotisation of the aromatic amino group and/or conversion into the corresponding hydrazine. Amino groups can also be activated by the introduction of reactive epoxide groups by reaction with bis-epoxides (e.g. 1,4-butanediol-diglycidyl ether) or epichlorohydrin. Details of such methods and other methods are described for example in Covalent and Coordination Immobilization of Proteins, Cabral J. M. S., Kennedy, J. F., in Protein Immobilization, Fundamentals and Application (Taylor R. F., publ.) Marcel Dekker Inc., 1991.

However, the activation of the amino groups on the carrier is preferably carried out by reaction with dialdehydes (e.g. glutardialdehyde). This method is particularly easy to carry out even in an aqueous medium. By this means it is possible to avoid the use of toxic compounds and organic solvents.

After the activation of the amino groups on the carrier, the enzyme is immobilized by contacting the activated carrier with the enzyme under suitable conditions. Subsequently non-reacted reactive groups of the carrier can be saturated. In the case of an aldehyde-activated carrier the saturation can be achieved for example with ethanolamine.

BRIEF DESCRIPTION OF THE DRAWINGS

FIG. 3 shows a comparison of the volume activities of immobilized glutaryl-7-ACA acylase for various carrier materials.

FIG. 4 shows a comparison of the flow properties of different column materials.

FIG. 5 shows a comparison of the compressibility of different column materials.

DESCRIPTION OF THE PREFERRED EMBODIMENTS

Figure 1:
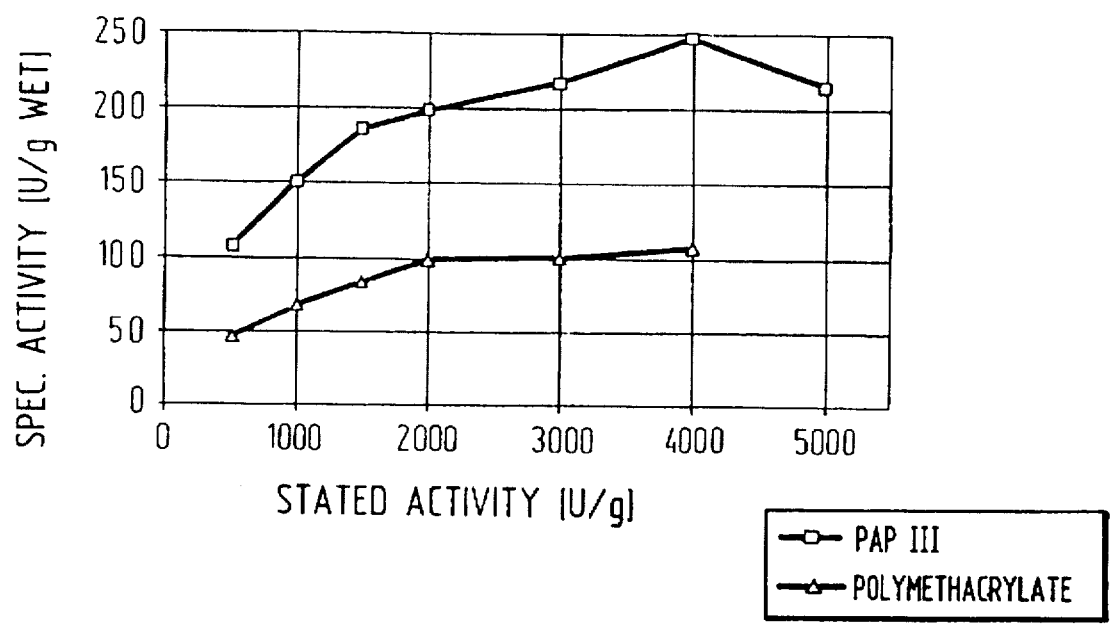
FIG. 1 shows a comparison of the specific volume activities of penicillin-G amidase which was immobilized on an amino-functionalized organopolysiloxane or on polymethacrylate.
Figure 2:
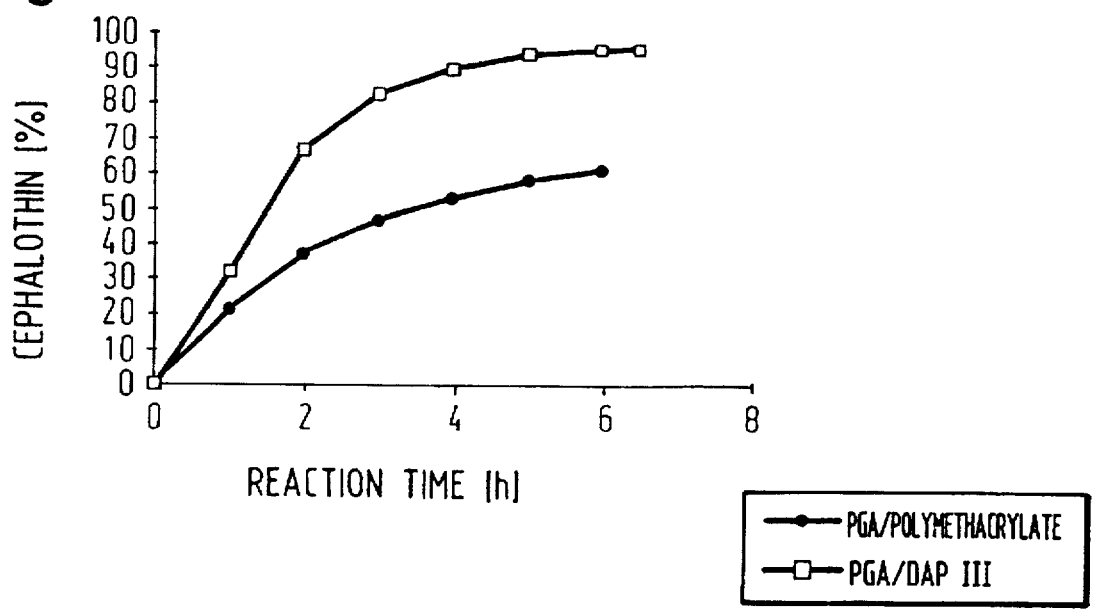
FIG. 2 shows a comparison of the product yield in a cephalothin synthesis using immobilized penicillin-G amidase which was immobilized on an amino-functionalized organopolysiloxane or on polymethacrylate.

In one embodiment the present invention concerns a penicillin-G amidase immobilized on a carrier. Penicillin-G amidase is an enzyme that is obtainable from a multitude of different bacterial species and some fungi and yeasts, preferably from E. coli. The weight ratio of penicillin-G amidase to carrier material is preferably in the range of 2 to 200 mg protein per g wet carrier, particularly preferably in the range of 40 to 80 mg protein per g wet carrier. In the immobilization of penicillin-G amidase on aminofunctional organosiloxane polymers according to the invention, specific volume activities can for example be achieved in the range of more than 100 U/g wet carrier and in particular of more than 125 U/g wet carrier. The specific volume activity is preferably in the range of 100 to 300 U/g wet carrier and particularly preferably in the range of 125 to 275 U/g wet carrier. The unit "U" for penicillin-G amidase is defined as the amount of enzyme which hydrolyzes 1 µmol penicillin G per minute under standard conditions (5% penicillin G, 0.6 mmol/l potassium phosphate buffer pH 8.0; 28° C.).

A further embodiment of the present invention concerns a glutaryl-7-ACA acylase immobilized on a carrier. Glutaryl-7-ACA acylase can for example be obtained from Acinetobacter spp. or from E. coli cells transformed with the glutaryl-7-ACA acylase gene (cf. EP-A-0 496 993). In the case of glutaryl-7-ACA acylase immobilized on a carrier the weight ratio of enzyme to carrier material is preferably in the range of 10 to 110 mg protein per g wet carrier, particularly preferably in the range of 20 to 70 mg protein per g wet carrier. The specific volume activity of a glutaryl-7-ACA acylase immobilized according to the invention can be more than 100 U/g wet carrier, in particular more than 125 U/g wet carrier. The specific volume activity of glutaryl-7-ACA acylase immobilized on a carrier is preferably in the range of 100 to 250 U/g wet carrier, particularly preferably in the range of 125 to 200 U/g wet carrier.

The unit "U" for glutaryl-7-ACA acylase is defined as the amount of enzyme that hydrolyzes 1 µmol 7β-(4-carboxybutan-amido)-cephalosporanic acid (glutaryl-7-ACA) per minute under standard conditions (2% Gl-7-ACA, 5 mmol/l potassium phosphate buffer pH 8.0; 37° C.).

Another embodiment of the present invention concerns D-amino acid oxidase immobilized on a carrier. The weight ratio of D-amino acid oxidase immobilized on a carrier to carrier material is preferably in the range of 5 to 25 mg protein per g wet carrier, particularly preferably in the range of 8 to 15 mg protein per g wet carrier. The specific volume activity of D-amino acid oxidase in the immobilization according to the invention can be 100 U/g wet carrier or more, in particular 125 U/g wet carrier or more. The specific volume activity is preferably in the range of 100 to 200 U/g, particularly preferably in the range of 125 to 175 U/g wet carrier. The unit "U" for D-amino acid oxidase is in this connection defined as a cephalosporin C (cephC) unit. The ceph-C activity is determined in the presence of catalase/$O_2/H_2O_2$. The amounts of products that are formed (α-ketoadipinyl-7-aminocephalosporanic acid and glutaryl-7-aminocephalosporanic acid) are quantified after separating the reaction solution by HPLC. An activity of 1 U corresponds to the formation of 1 µmol products/min at 25° C. under standard conditions (1.3 kU catalase, $O_2$-saturated solution, 0.007% $H_2O_2$).

If desired, the D-amino acid oxidase can also be present coimmobilized with catalase (E.C.1.11.1.6). In this case 50 U–100 U catalase per U (ceph-C U) D-amino acid oxidase is generally used. The immobilization of the catalase is carried out according to the techniques described above. The activity of 1 U catalase corresponds to the amount of enzyme that hydrolyzes 1 µmol $H_2O_2$ per minute under standard conditions (25 mmol/l potassium phosphate buffer pH 7.0; 0.018% $H_2O_2$).

The D-amino acid oxidase according to the invention is obtainable from a large number of organisms e.g. E. coli, Pseudomonas species, Aerobacter species, Candida tropicalis, Penicillinium roqueforti, Aspergillus flavus and Aspergillus niger, Neurospora crassa, Nocardia, Citrobacter, Rhodotorula and Trigonopsis variabilis. The D-amino acid oxidase from Trigonopsis variabilis is particularly preferred. The isolation and purification of this enyzme is described for example in EP-A-0 211 033.

The present invention also concerns the use of enzymes immobilized on carriers according to the invention individually or in combinations of at least two of the said enzymes in an enzymatic synthesis reaction. Penicillin-G amidase can for example be used in the synthesis of cephalothin from 7-ACA and thienylacetic acid. D-Amino acid oxidase and glutaryl-7-ACA acylase can be used in the two-step enzymatic synthesis of 7-ACA from cephalosporin C.

The enzymes immobilized on carriers according to the invention differ from known enzymes immobilized on carriers by their increased volume activity, increased stability or/and improved mechanical properties of the immobilisate. The present invention therefore also concerns a process for improving the volume activity of enzymes immobilized on carriers selected from the group comprising penicillin-G amidase (E.C.3.5.1.11), glutaryl-7-ACA acylase and D-amino acid oxidase (E.C.1.4.3.3) which is characterized in that the enzyme is immobilized by covalent binding on an aminofunctional organosiloxane polymer carrier material.

As described above the immobilization of the enzymes on the carrier material is preferably carried out by means of a dialdehyde e.g. glutardialdehyde, but all other methods suitable for the immobilization of proteins on aminofunctional carriers can also be used.

Surprisingly the enzymes immobilized on carriers according to the invention exhibit high volume activities by means of which high product yields can be achieved in industrial synthesis reactions. The immobilized enzymes according to the invention are particularly suitable in reactions in which low temperatures e.g. 4°–30° C. predominate or/and organic solvents such as dimethylformamide, dimethylsulfoxide etc. are present. Furthermore the immobilized enzymes according to the invention exhibit improved mechanical properties compared to other carrier materials, such as suitability for columns and compressibility.

The following examples in conjunction with FIGS. 1 to 5 are intended to further elucidate the present invention.

EXAMPLES

Example 1

Production of immobilized penicillin-G amidase

Amino-functionalized organopolysiloxanes with various specifications were obtained from the DEGUSSA AG. The functional groups of the individual substances are shown in the following Table 1:

TABLE 1

| Material | Capacity mval/g | Capacity mval/ml | Particle size mm | Functional group |
|---|---|---|---|---|
| PAP III | 3.14 | 0.66 | 0.1–0.3 | —$NH_2$ |
| DAP III | 2.77 | 0.49 | 0.1–0.3 | —NH—$(CH_2)_2$—$NH_2$ |
| DAP IV | 1.7 | 0.34 | 0.2–0.4 | —NH—$(CH_2)_2$—$NH_2$ |

1 ml of a 25% glutardialdehyde solution in 0.1 mol/l potassium phosphate buffer pH 7.0 was added to 1 g PAP III carrier material containing amino groups and stirred for 1 hour at room temperature with a propeller mixer. The treated gel is washed with 20 ml 0.1 mol/l potassium phosphate buffer solution pH 7.0. 500–5000 U of a penicillin-G amidase solution in 10 ml 0.01 mol/l potassium phosphate pH 7.0 is added to the activated carrier material and the suspension is stirred for 2 hours at room temperature. Excess reactive groups are saturated with 1 ml 0.1 mol/l ethanolamine solution pH 9.0 by stirring for one hour at room temperature.

Subsequently it is firstly rinsed at 4° C. with 50 ml 0.02 mol/l potassium phosphate buffer pH 7.0/1 mol/l NaCl and then with 50 ml 0.02 mol/l potassium phosphate buffer. Activity determinations of the coupling and wash solutions as well as of the immobilized enzyme are carried out under pH stat conditions on an autotitrator (5% penG, 28° C., pH 8.0, 0.6 mol/potassium phosphate buffer). Details of the specific activity are based on the wet weight of the catalyst.

The specific volume activities of PAP III and polymethacrylate derivatives are compared in FIG. 1.

The high volume activities that can be obtained with the carriers according to the invention enable the immobilized penicillin-G amidase (PGA) to be used in synthesis reactions in which low temperatures and pH values as well as organic solvents are necessary for high product yields. Equilibrium syntheses of cephalothin from 7-ACA and thienylacetic acid with the same volume of immobilized PGA and using PAP III and polymeth-acrylate-immobilized PGA are compared in FIG. 2.

Example 2

Immobilization of glutaryl-7-ACA acylase

The immobilization is carried out analogous to the PGA immobilization. 180–250 U/g wet carrier material DAP III or PAP III is used. The resulting volume activities are shown in FIG. 3 in comparison to polymethacrylate and nylon-immobilisates.

Example 3

Immobilization of D-amino acid oxidase (DAO)

The enzyme is dialyzed against 20 mmol/l $KPO_4$ buffer pH 7.0/1 mmol/l dithiothreitol before the immobilization. 2500 U DAO (D-alanine units) are added per g wet carrier material DAP III. The excess reactive sites are blocked by stirring for 1 hour with 0.1 mol/l ethanolamine solution pH 8.0. The washing is carried out with 0.5 mol/l NaCl/0.2 mmol/l DTT/0.5 mmol/l EDTA in sdcx 20 mmol/l $KPO_4$, pH 7.0. Activities of >1000 U/g wet carrier material are obtained.

Table 2 shows the volume activities of immobilized DAO using various carrier materials.

TABLE 2

| Carrier material | DAP III | Polymethacrylat/ decylamine | Chitosan | Wofatit ® | Duolite 762 | ES XAD 2 | XAD 8 | Acryl amide |
|---|---|---|---|---|---|---|---|---|
| Loading [D-Ala U/g] | 2500 | 1660 | 2500 | 5000 | 3000 | 3000 | 3000 | 666 |
| Volume activity [Ceph-C U/g] | 150 | 76 | 44 | 40 | 0 | 0 | 11 | 4 |

D-Ala activity: The activity of D-amino acid oxidase is determined with D-alanine as the substrate in the presence of catalase/$H_2O_2$/lactate dehydrogenase/NADH at 25° C. (cf. Biochemicals for the diagnostic industry and clinical chemistry, 1993/94, 5th ed., p. 25, Boehringer Mannheim GmbH, Mannheim Germany)
Ceph-C activity: The activity with cephalosporin C is determined in the presence of catalase/$O_2$/$H_2O_2$. The amounts of products formed (α-ketoadipinyl-7-aminocephalosporanic acid and glutaryl-7-aminocephalosporanic acid) are quantified after separating the reaction solution by HPLC. An activity of 1 U corresponds to the formation of 1 μmol products/min at 25° C.
XAD 2: Carrier material on polystyrene basis
XAD 8: Carrier material on acrylic acid basis

Example 4

Mechanical properties

1. Flow properties/suitability for columns

The filtration properties of various carrier catalysts (Eupergit C, polyacrylamide gel, PAP III) are determined by measuring the flow volume/unit of time at constant hydrostatic pressure and identical gel bed height. The experiment is repeated twice without prior gel relief. The result of this experiment is shown in FIG. 4. It is apparent that the aminofunctional polysiloxane has better flow properties than the other carrier materials.

2. Compressibility

The compressibility of organopolysiloxane PAP III as well as Eupergit and polyacrylamide were determined in a column flow test using the same gel bed volumes and filling heights. FIG. 5 shows the dependence of the linear flow rate on the hydrostatic pressure. It is apparent that the aminofunctional polysiloxane has better compressibility properties than the other carrier materials.

We claim:

1. An emmobnilized enzyme comprising an enzyme selected from the group consisting of penicillin-G amidase, glutaryl-7-ACA acylase and D-amino acid oxidase immobilized by covalent binding to an aminofunctional organosiloxane polymer carrier material having an average diameter of 0.01 to 3 mm wherein the enzyme has a specific volume activity of at least 100 U/g carrier material.

2. The immobilized enzyme as claimed in claim 1, wherein
the enzyme is immobilized on the carrier material by means of a dialdehyde.

3. The immobilized enzyme as claimed in claim 1, wherein
the weight ratio of enzyme to carrier material is in the range of 1 to 300 mg protein per g wet carrier.

4. The immobilized enzyme as claimed in claim 1, wherein
the average particle size of the carrier material is 0.1 to 0.4 mm.

5. The immobilized enzyme as claimed in claim 1, wherein
the carrier material is essentially spherical.

6. The immobilized enzyme as claimed in claim 1, wherein the enzyme is penicillin-G amidase and
the weight ratio of enzyme to carrier material is in the range of 2 to 200 mg protein per g wet carrier.

7. The immobilized enzyme as claimed in claim 6, wherein
the weight ratio of enzyme to carrier material is in the range of 40 to 80 mg protein per g wet carrier.

8. The immobilized enzyme as claimed in claim 6, wherein
the specific volume activity is in the range of 100 to 300 U per g wet carrier.

9. The immobilized enzyme as claimed in claim 1, wherein the enzyme is glutaryl-7-ACA acylase and
the weight ratio of enzyme to carrier material is in the range of 10 to 110 mg protein per g wet carrier.

10. The immobilized enzyme as claimed in claim 9, wherein
the weight ratio of enzyme to carrier material is in the range of 20 to 70 mg protein per g wet carrier.

11. The immobilized enzyme as claimed in claim 9, wherein
the specific volume activity is in the range of 100 to 250 U per g wet carrier.

12. The immobilized enzyme as claimed in claim 1, wherein the enzyme is D-amino acid oxidase and
the weight ratio of enzyme to carrier material is in the range of 5 to 25 mg protein per g wet carrier.

13. The immobilized enzyme as claimed in claim 12, wherein
the weight ratio of enzyme to carrier material is in the range of 8 to 15 mg protein per g wet carrier.

14. The immobilized enzyme as claimed in claim 12, wherein
the specific volume activity is in the range of 100 to 200 U per g wet carrier.

15. The immobilized enzyme claimed in claim 12, wherein
the enzyme is co-immobilized with catalase.

16. A method of synthesizing a modified penicillin or cephalosporin antibiotic comprising synthesizing the antibiotic in a reaction catalyzed by an immobilized enzyme as claimed in claim 1.

17. The method as claimed in claim 16, wherein
the reaction is carried out at a temperature of to 30°.

18. The method as claimed in claim 16, wherein
the reaction takes place in the presence of an organic solvent.

19. A process of preparing an immobilized enzyme comprising immobilizing an enzyme selected from the group consisting of penicillin-G amidase, glutaryl-7-ACA acylase and D-amino acid oxidase, comprising on an aminofunctional organosiloxane polymer carrier material having an average particle diameter of 0.01 to 3 mm by covalent binding to provide an immobilized enzyme having a specific volume activity of at least 100 U/g wet carrier material.

20. The process as claimed in claim 19, wherein
immobilizating of the enzyme on the carrier material is achieved by means of a dialdehyde.

21. The process as claimed in claim 19, wherein
the weight ratio of enzyme to carrier material is in the range of 1 to 300 mg protein per g wet carrier.

22. The process as claimed in claim 19, wherein
a carrier material with an average particle size of 0.1 to 0.4 mm is used.

23. The process as claimed in claim 19, wherein
a spherical carrier material is used.

* * * * *

UNITED STATES PATENT AND TRADEMARK OFFICE
CERTIFICATE OF CORRECTION

PATENT NO. : 5,780,260
DATED : July 14, 1998
INVENTOR(S) : Wedekind et al.

It is certified that error appears in the above-identified patent and that said Letters Patent is hereby corrected as shown below:

Title page, item [22], delete "Dec. 13, 1996" insert therefor --Dec. 13, 1994--.

Signed and Sealed this

Fifteenth Day of September, 1998

Attest:

BRUCE LEHMAN

Attesting Officer     Commissioner of Patents and Trademarks